United States Patent [19]

Long

[11] Patent Number: 5,642,198
[45] Date of Patent: Jun. 24, 1997

[54] METHOD OF INSPECTING MOVING MATERIAL

[76] Inventor: William R. Long, R.D. #1 373 B, Smithfield, Pa. 15478

[21] Appl. No.: 415,944

[22] Filed: Apr. 3, 1995

[51] Int. Cl.$^6$ ..................................................... G01N 21/88
[52] U.S. Cl. ............................................. 356/430; 356/239
[58] Field of Search ................................... 356/239, 237, 356/430, 431, 371; 250/559.04, 559.05

[56] References Cited

U.S. PATENT DOCUMENTS

| | | |
|---|---|---|
| 3,533,706 | 10/1970 | Maltby, Jr. et al. . |
| 3,792,930 | 2/1974 | Obenreder .................. 356/371 |
| 4,330,712 | 5/1982 | Yoshida . |
| 4,448,526 | 5/1984 | Miyazawa . |
| 4,448,532 | 5/1984 | Joseph et al. ............. 356/394 |
| 4,461,570 | 7/1984 | Task et al. . |
| 4,492,477 | 1/1985 | Leser . |
| 4,634,281 | 1/1987 | Eikmeyer . |
| 4,647,197 | 3/1987 | Kitaya et al. . |
| 4,656,360 | 4/1987 | Maddox et al. . |
| 5,068,799 | 11/1991 | Jarrett ...................... 356/430 |
| 5,128,550 | 7/1992 | Erbeck . |
| 5,157,266 | 10/1992 | Schmiedl . |
| 5,220,178 | 6/1993 | Dreiling et al. ............. 356/430 |
| 5,440,648 | 8/1995 | Roberts et al. ............. 356/430 |

*Primary Examiner*—Richard A. Rosenberger
*Attorney, Agent, or Firm*—Diller, Ramik & Wight, PC

[57] ABSTRACT

This disclosure is directed to a glass inspection system for inspecting a transparent web of glass of indeterminate length as it moves along a predetermined linear path of travel at a predetermined, regulated and/or controlled speed. The web of glass is illuminated such that any defect in or upon the glass web appears as a shadow moving upon a relatively white/bright background. A number of high resolution CCD cameras "look" downwardly through the transparent glass web and are focused upon the white background to detect moving defect shadows. Each camera creates a succession of image fields or frames through which a shadow of a defect will pass as the defect moves with the glass web through the scan area of each CCD camera. Each image field defines a nominal light area and each defect shadow is depicted as a defect area of light differing from the nominal light of each image field area. Initially, a first image area is scanned to detect the presence of a first light area/shadow at a first position which might be indicative of a defect shadow created by an "apparent" defect moving with the transparent glass web. Subsequently, a second image field is scanned at a second predetermined position to detect the presence of the first defect light area or shadow at the downstream second position commensurate with the speed of movement of the transparent glass body. If the first defect light area detected at the first position is present and is detected at the downstream second position, the latter confirms the existence of the defect, as opposed to the possibility of a spurious first scan, dirt rather than a defect on or in the glass, etc.

31 Claims, 3 Drawing Sheets

METHOD OF INSPECTING MOVING MATERIAL

BACKGROUND OF THE INVENTION

The invention relates to a method of inspecting moving material, and though specifically directed to a process for inspecting a transparent web of glass of indeterminate length to detect flaws, contaminants, defects or similar foreign bodies thereon or therein as the transparent glass web is being manufactured by a conventional float glass process, the invention is equally applicable to inspecting individual transparent bodies, such as individual sheets of transparent glass, as well as opaque webs of indeterminate length, and/or individual opaque bodies. Thus, while the present invention is specifically directed to the manufacture of a transparent float glass web or sheet, the invention is equally applicable to the inspection of virtually any transparent or opaque product, including but not limited to opaque webs of tin plate, steel, aluminum foil or the like, virtually any type of transparent or opaque polymeric/copolymeric synthetic plastic films, individual sheets of glass or virtually any body upon or in which flaws or defects might reside. However, since the invention has been reduced to practice with respect to the inspection of float glass webs, the specification shall be primarily directed to the latter process without, of course, limitations upon the eventual products capable of being inspected for any of a variety of flaws or defects.

A glass inspection system associated with the production of float glass is disclosed in U.S. Pat. No. 4,492,477 in the name of Jacques F. Lesser granted on Jan. 8, 1985. This patent makes mention of the difficulty of distinguishing between glass defects and soil or foreign bodies present on the surface of a float glass sheet, and seeks to discriminate between flaws of the glass material itself, such a bubbles, drops, inclusions and projections of tin, for example, which effect the flatness and transparency of the glass, as opposed to simple dirt on the glass surface which can be washed away. The patent recognizes the conventionality of utilizing laser beams and infrared in conventional glass inspection systems, as well as the supposed disadvantages thereof, such as perfect synchronization, constant velocity, high cost of use, and high risk of deterioration. The patentee found that any flaws in the glass, be it bubbles, blow holes, drops or even partial inclusions, causes flatness defects on the glass surface. By illuminating the glass the deviation of the luminous rays caused by flaws renders the image thereof more luminous than the general image of the source of light. This deviation is attained by the effective of refraction in the mass of the deformed glass, and thus glass deformation as an overall defect can be distinguished from simple soiling. The inspection system includes a source of light located on one side of the sheet of glass and a photosensitive sensor located on an opposite side of the sheet of glass. A flaw causes a deviation of the beam of light which passes through the glass sheet to refract the light creating a bright image at the sensor which indicates the presence of a flaw, whereas soil or dirt simply causes the beam of light to darken. The inspection system also includes a plurality of light sources associated with a plurality of sensors for scanning sections of the glass with a slight overlap in adjacent scan areas. A camera is associated with each scan area and includes associated optics, photodiodes and circuitry to detect flaw signals which are subsequently compared with information stored in buffers for eventually cutting the glass to remove defects.

U.S. Pat. No. 5,157,266 granted on Oct. 20, 1992 to Roland Schmiedel discloses another method of inspecting transparent sheets or webs for the presence of defects, particularly enclosed core seeds, by utilizing a flying light spot. The flying light spot directs light through the glass web to a receiver which has transparent and opaque regions. When the light passes through a glass web which is free of defects, the light spot covers the transparent and opaque regions in a continuous alternating fashion of regular pulses, but any defects in the glass create a fluctuation in these pulses indicating the presence of a defect.

Another process for detecting the presence of defects on a moving sheet of glass is disclosed in U.S. Pat. No. 5,220,178 in the name of Mark J. Dreiling et al. granted on Jun. 15, 1993. Light from a light source passes through a dark (black) background slit and the glass sheet and is detected by a camera coupled to a computer. Speck defects and fisheye defects act as optical lenses and appear darker than the dark background and are thereby distinguishable.

In U.S. Pat. No. 3,533,706 in the name of Robert E. Maltby, Jr. et al. granted on Oct. 13, 1970 glass is inspected for defects by utilizing light rays passing through the glass and discriminating glass defects from dust and/or dirt and/or water by the angle of light deviation. A sensor produces a signal as a function of the intensity of the light which indicates the severity of the defect. Defects in the glass will scatter the light rays whereas if there are no defects in the glass the light rays will not be scattered, and the latter achieves the desired discrimination.

U.S. Pat. No. 4,461,570 in the name of Harry L. Task et al. granted on Jul. 24, 1984 and U.S. Pat. No. 4,647,197 in the name of Katsuhiki Kitaya et al. granted on Mar. 3, 1987 each disclose the utilization of a camera to inspect a transparent glass windshield by sighting through the windshield upon a target and determining the presence or absence of defects in the glass by the pulse generated from the target. Defective (distorted) glass will create a target pulse different from acceptable glass.

SUMMARY OF THE INVENTION

In its broadest aspects, the inspecting method of the present invention is utilized in conjunction with either opaque or transparent bodies, such as a web or section of steel or tinplate on the one hand or a web or a section of transparent glass on the other hand. In each case the body is moved along a predetermined path of travel in a predetermined direction at a predetermined speed and light is directed toward the body which is assumed to have a defect therein or thereupon. In the case of an opaque body, the light is reflected from the defect and the detected light is indicative of a first defect location at a first position of body movement along the predetermined path of travel. Subsequently, the presence of the same defect upon the body is detected at a second position of body movement downstream of the first position. The existence of the second defect location at the second position thereby confirms the existence of the defect due to its movement from the first defect detecting location to the second defect detecting location. If, on the other hand, the first defect detected at the first position is not detected at the second position, there is no corroboration of the defect detected at the first position and the conclusion is that the first defect detection was spurious and the body is devoid of defects. Essentially, this inspection system takes a minimum of two "looks" at two different times and if the system "sees" the same thing twice, the second "look" confirms the first "look" and this confirmation establishes the presence or a defect. However, if the first "look" is not confirmed by a positive second "look," there is no confirmation and, thus, there is no defect.

When the latter inspection method is utilized in conjunction with a moving transparent body, the defect on or in the transparent body is not directly detected, but instead light rays pass through the transparent body entering a first side, exit a second side, and impinge upon a white background. A defect on or in the transparent body will cast a shadow upon the white background, and it is the presence or absence of the shadow which is indicative of the presence or absence of a defect. As in the case of an opaque body, the presence or absence of a shadow is detected at a first location, and the presence of a defect is sensed as a first shadow upon the background. Subsequently, the presence of the same shadow upon the background is sensed at a second position of body movement downstream from the first position. If the second shadow is detected at the second shadow location at the second position, the existence of the second shadow confirms the existence of the first shadow and thus confirms the existence of a defect of the transparent body.

The inspecting system just described is very simple and straightforward, particularly when compared to the conventional inspection processes described earlier, and the only possible variable in the inspection system which is highly controllable is the speed of movement of the body under inspection. However, the speed of body movement is readily determined and controlled and once established and maintained, there is a specific time incriminate for an apparent defect to travel a predetermined incremental distance between the first detection for a defect at the first position and the second detection of the defect at the second downstream position. If the first detection establishes an "apparent" defect at the first defect location, this defect will arrive at a predetermined incremental time period at the second position and will be detected thereat, thereby confirming the existence of a defect. If, however, the first "apparent" defect is a spurious detection, such as sensing/ circuitry malfunction, a like spurious detection at the second position would not occur and the absence of a defect at the second defect detecting location would thereby not confirm the existence of a defect at the first detection position. As another example, if the first "apparent" defect were merely a piece of dirt, be it upon or a reflection from an opaque body or dirt on the white background associated with a transparent body, most likely the first "apparent" defect upon the body would shift in its position because of body movement, whereas dirt upon the white background would not move at all. In both cases, the time differential between the first and second detection positions would preclude confirmation thereby confirming the nonexistence of a defect.

In the utilization of the present method to inspect a transparent web of glass of indeterminate length leaving the cold end of a float glass furnace, the web of glass moves along a predetermined linear path of travel at a predetermined, regulated, controlled, detected and/or known speed. The web of glass is illuminated such that any defect in or upon the glass web appears as a shadow moving upon a relatively white/bright background. A number of high resolution CCD cameras scan downwardly through the transparent glass web and are focused upon the white background to detect moving defect shadows. In actual practice four such CCD cameras are utilized to simultaneously scan the entire width of the transparent glass web with the scanning width of adjacent cameras being in slightly overlapped relationship to assure scanning reliability. Each camera acquires a succession of image fields or frames through which a shadow of a defect will pass as the defect moves with the glass web through the scan area of each CCD camera. Each image field defines a nominal light area and each defect shadow will be depicted as a defect area of light differing from the nominal light of each image field area. Initially, an acquired first image area is scanned to detect the presence of a first defect light area/shadow at a first position which might be indicative of a defect shadow created by an "apparent" defect moving with the transparent glass web. Subsequently, a second acquired image field is scanned at a second predetermined position to detect the presence of the first defect light area/shadow at the downstream second position at which it would arrive commensurate with the speed of movement of the transparent glass web. If the first defect light area detected at the first position is present at the downstream second position, the latter confirms the existence of a defect, as opposed to the possibility of a spurious first scan, dirt rather than a defect on the glass which might move as the transparent glass web travels, etc. Accordingly, at a minimum of two scans at two different positions of two acquired image fields or frames a relatively high degree of reliability can be achieved to distinguish glass defects from non-defects, spurious signals or the like.

Preferably, the inspection method also includes a third scan of a third image field at a third position downstream of the second position, once again to determine whether the first defect light area/shadow arrived at the third scanned position at a time commensurate with the speed of travel of the transparent glass web. If the third scan is positive, the existence of the first defect light area at the third position of scan is further confirmation of the existence of the defect in or upon the glass web, as opposed to a spurious signal, etc.

In further accordance with the present invention, each image field is created by a pixel area corresponding to the frame acquired by each CCD camera, and each scanning step is performed by scanning a limited pixel area or group of each acquired pixel area image field or frame by initiating scanning at a downstream leading edge or pixel line of each limited pixel area and continuing the scanning of each limited pixel area in an upstream direction. This leading edge or bottom-up limited pixel area scanning approach increases the scanning speed of the inspection method absent any decrease in the reliability thereof.

The inspection method also confirms the existence of a defect in the glass web by scanning for what might be best termed the "ghost" of the first defect light area at the first position at a time subsequent to the initial scan and preferably at a time during which the scan is being conducted at the second position. Obviously, as the glass web moves, the first defect light area scam-scanned at the first position will also move and if this same area is subsequently scanned, the first defect light area would be absent ("ghost") which further confirms the existence of a defect through the absence of the first defect light area at the first scanned position during a subsequent scan thereof.

In further accordance with the inspection method of the present invention, a number of other aspects of each defect light area are analyzed not only to establish the existence of a defect but the specifics thereof. As examples, the defect light area represented as a pixel array is analyzed by at least one of (a) determining the ratio of light change between the first defect light area and the nominal light area of the associated image field;

(b) determining the size area of the first defect light area;

(c) determining the length and width of the first defect light area;

(d) determining the number of bright peaks and light peaks of the first defect light area; and (e) determining the sharpness of the first defect light area.

The latter analyzes of a defect light area or pixel array is utilized in conjunction with appropriate artificial intelligence to determine the specific type of defect involved and distinguish one defect from another, such as stones, tin drip, bubbles, dross, seeds, lip scar, roll marks, ream, markable ream, white tin, black tin, elemental tin, etc. Depending upon the eventual end use of the glass, some defects are acceptable, while others are not, and therefore by determining the specific type defect, the inspection system can be utilized to sort glass sections eventually cut from the glass web based upon end use and the specifics of associated defects.

With the above and other objects in view that will hereinafter appear, the nature of the invention will be more clearly understood by reference to the following detailed description, the appended claims and the several views illustrated in the accompanying drawings.

DESCRIPTION OF THE PREFERRED EMBODIMENT

A novel inspection method of the present invention will be described in conjunction with FIG. 1 of the drawings, illustrating an inspection apparatus 10 associated with the inspection of glass during its manufacture by a conventional "float glass" process during which molten glass floats on a bath of molten tin, exits a float glass furnace as a continuous glass web of indeterminate length, and is conveyed by knurled edge drive rollers along underlying conveyor rollers toward, beneath and beyond an inspection booth 11.

Figure 1:
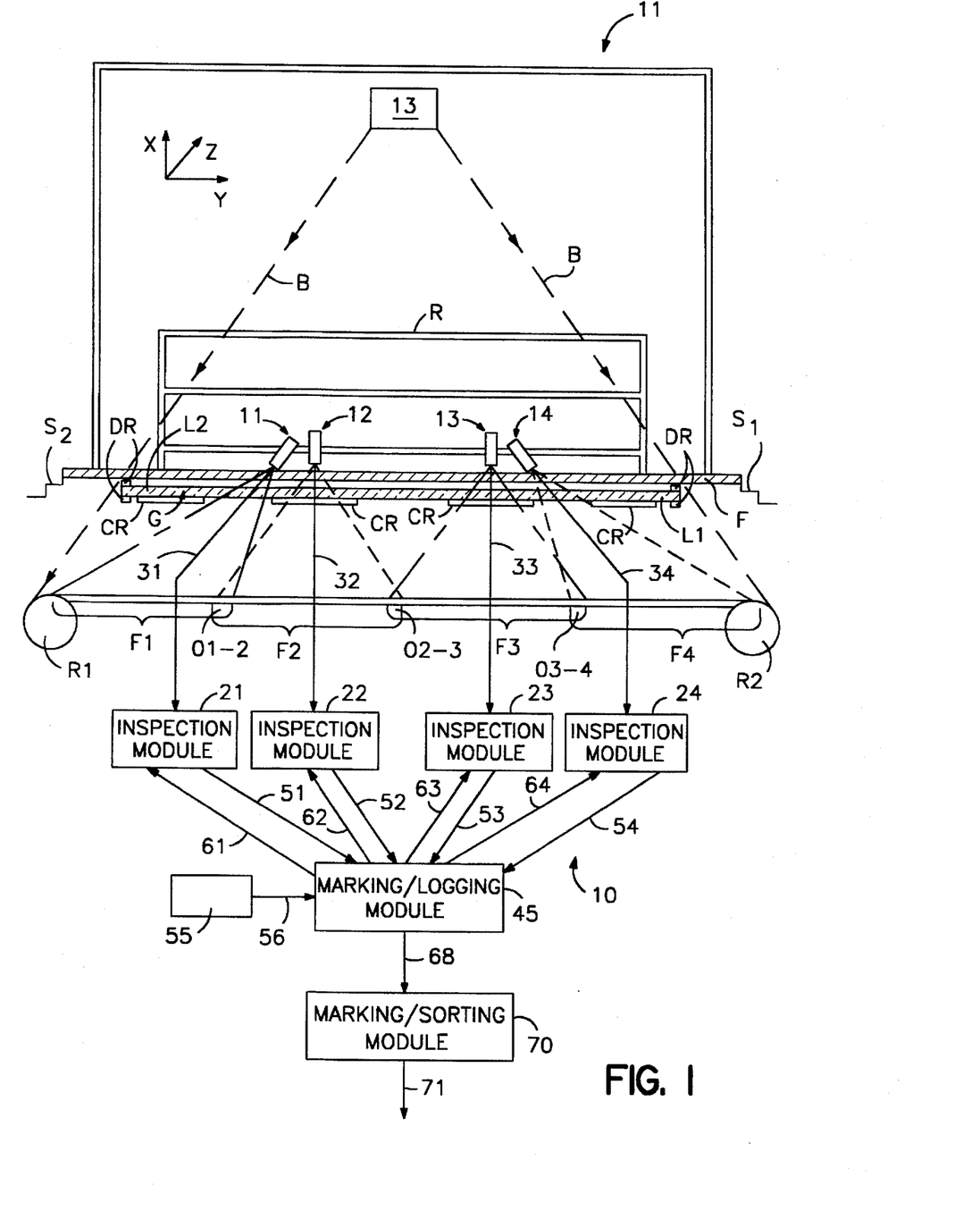
FIG. 1 is a schematic view taken transverse to an inspection booth associated with a float glass furnace, and illustrates a light source directing light through a transparent web of glass and impinging upon an underlying white background upon which is focused CCD cameras with adjacent scanning fields thereof being in slightly overlapped relationship: inspection modules; marking and logging modules; and an associated marking/sorting module for effecting glass web cutting and sorting.

A web of transparent glass G is illustrated in FIG. 1 exiting the float glass furnace (not shown) travelling in the "z" direction away from the reader beneath a floor F of the inspection booth 11 which houses one or more human inspectors. The floor F has a transverse opening (not shown, but extending in the "y" direction) through which the inspectors can view the underlying moving web of glass G as it exits the float glass furnace. The glass web G is supported by a series of transversely underlying conveyor rollers CR and is conveyed by synchronously driven knurled drive rollers DR at opposite longitudinal edges L1, L2 of the glass web G. A railing R in the inspection booth 11 assures that an inspector will not accidentally step through the transverse opening of the floor F while walking along or across the floor F or entering or exiting the inspection booth 11 which can be achieved through opposite doorways (not shown) accessed by appropriate stairs S1, S2.

The inspection booth 11 is relatively dim but does include a conventional light source 13 which directs a bright beam of light B downwardly through the opening in the floor F through the glass web G and upon a stationary brightly lit white background W. The stationary white background W is preferably a sheet of bright white paper which traverses and projects appreciably beyond the opposite longitudinal edges L1, L2 of the glass web G. The bright white sheet of paper W can be between 4'-8' in the direction "z" of glass web movement for facilitating manual inspection, although the white paper sheet W can be relatively narrower for automated inspection in keeping with the present invention. The white paper sheet W is preferably drawn from a fresh roll R1, utilized in a stationary fashion during the performance of the inspection process, but at selected time intervals as dirt or debris might accumulate upon an upper surface of the white sheet W, a fresh portion is drawn from roll R1 while the prior soiled portion is wound upon a take-up roll R2 to maintain a relatively clean white background W for both manual and automatic inspection.

During manual inspection, an inspector simply looks clown through the opening in the floor F and, as the glass web G passes by, the inspector continuously scans the glass web looking for defects, such as stones, tin drip, bubbles, etc. When a defect is visually apparent to the inspector, the defect is marked by the inspector marking the glass adjacent the defect with a marking "wand" which is a relatively long rod having a handle end and a marking end with the latter including a wick or brush which can be dipped, as necessary, into an appropriate liquid marking medium. While the human inspection process is viable, it is limited by human capabilities. The inspector has limited visual capabilities, no multi-direction capability and a very short attention span.

In lieu of manual inspection, the present invention utilizes as part of the inspection apparatus 10 process four identical CCD camera means 11–14 each in the form of a high resolution (768(H)×493(V)) CCD shutter camera, such as the PULNiX TM 7453E high resolution shutter camera manufactured by PULNiX America Inc. of 1330 Orleans Drive. Sunnyvale. Calif. 94089, which are focused to scan upon respective transverse scanning fields F1–F4 with transversely adjacent scanning fields being in slightly overlapped scanning relationship, as indicated by overlapped scanning field portions 01–2, 02–3 and 03–4. The white background W is positioned approximately three feet below the glass web G and any defect, such as stones, tin drip, bubbles, seeds or the like on or in the glass web G, will appear as a moving defect shadow upon the white background W upon which the cameras 11–14 are focused. Accordingly, any defect anywhere in the glass web G will be reproduced as a defect shadow somewhere across the transverse width of the background W and will encounter at least one of the scanning fields F1–F4 and/or the overlapping scanning field portions 01–2, 02–3 and 03–4. Therefore, as the glass web G proceeds to, through and beyond the scanning fields F1–F4 beneath the cameras 11–14, a shadow of a defect (defect shadow) travelling along the white background W will be acquired by at least one of the cameras 11–14 as a defect area of light differing in intensity from the nominal light of each of a series of successively acquired image fields or frames. These image fields or frames are fed to respective inspection module means 21–24 conventionally connected at 31–34 to the respective cameras 11–14.

Each inspection module 21–24 is a conventional desk-top computer, such as Model VLB ISA 486-DX2-66 manufactured and sold by BSI of 9440 Tellstar Avenue, El Monte, Calf. 91731 which includes an internal imaging board functioning as a frame grabber that allows each inspection module or computer 21–24 access to the scanned/acquired image fields or frames of the respective cameras 11–14. Each inspection module 21–24 uses an imaging board manufactured by Epix, Inc. of 3005 MacArthur Blvd., Northbrook, Ill. 60062-19011.

Figure 2:
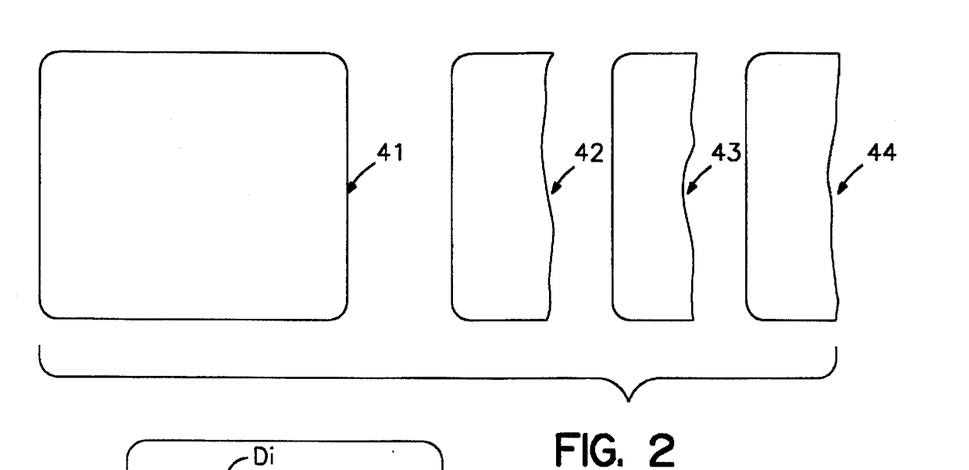
FIG. 2 is an exploded fragmentary view of an image area or frame of each of the CCD cameras, and illustrates one of many successively acquired image fields or frames which are successively scanned to detect apparent defects and confirm the existence of actual glass defects.

An image field or image area grabbed or acquired by the CCD cameras 11–14, absent the detection of a defect shadow, are designated respectively 41–44 in FIG. 2. Each image field 41–44 is of the same nominal brightness because in any one acquired no-defect image field, the background W is white and there are no disturbances (defects) as sequences of frames are acquired by each of the cameras 11–14 as the glass web G passes beneath the cameras 11–14. Therefore, so long as there is no change upon the white background W between successively acquired image fields 41–44 the constant nominal brightness of succeeding image fields indicates that no shadow defects have been observed, and hence the glass web G is thus far defect free. The image fields 41–44 each represent the total pixel area of each frame acquired successively by each of the cameras 11–14, and so long as there is no change in the nominal pixel area brightness from successive frame to successive frame, nothing further occurs because under such conditions the glass web G is defect free. If, however, any one of the image fields 41–44 reflects a change in the nominal brightness thereof during a scan of its associated image field, the latter reflects the possibility of a defect ("apparent") in or upon the web of glass G.

Figure 3A:
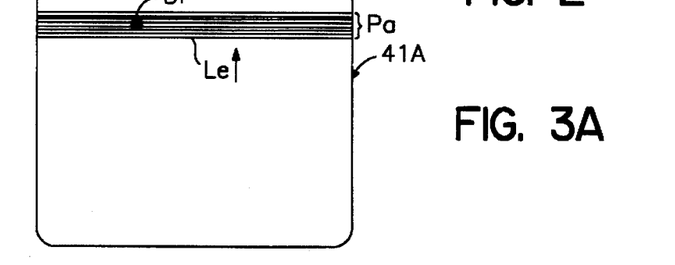
FIG. 3A, FIG. 3B and FIG. 3C are successive image fields of one of the CCD cameras, and successively illustrate three scans at three different positions in the downstream direction of transparent glass web travel which are utilized to confirm the existence of a defect as well as the specific nature thereof.
Figure 3B:
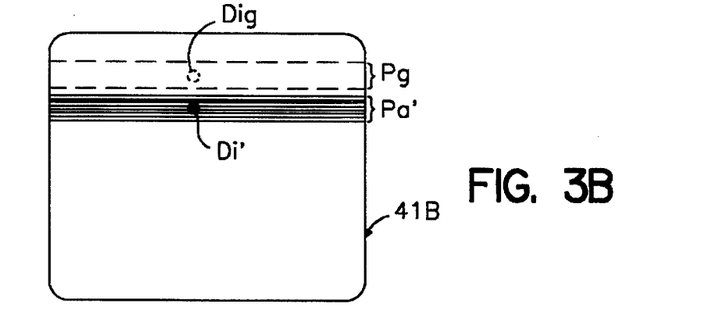
Figure 3C:
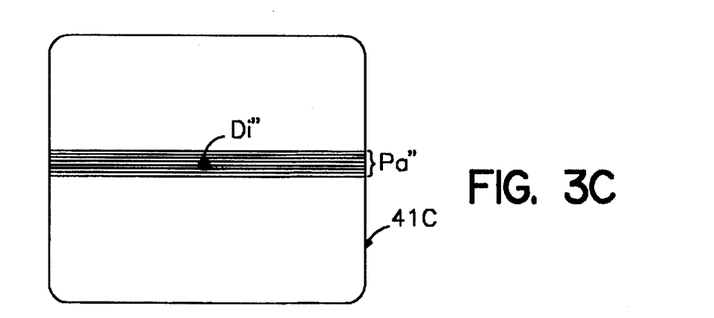

Reference is made to FIGS. 3A through 3C which depict three image fields or image areas 41A through 41C successively acquired and scanned by the camera 11 and its associated inspection module 21. Similar successively acquired image fields or areas (not shown) are also acquired by the cameras 12–14, but since the cameras 11–14 and the inspection modules 21–24 operate identically, the description of the operation of the camera 11 in association with the inspection module 21 and the image areas 41A–41C will simplify an understanding of the invention.

When a shadow defect is detected during a scan of a subsequently acquired frame/image field by any one of the cameras 11–14, there is a change in the light background W created by the darker shadow defect which triggers a marking and logging module 45 associated with each particular camera 11–14. Unlike current laser and line scan CCD systems which scan a single line at a time, in keeping with the present method a limited pixel area or array Pa of each image field 41, 41A, etc. is scanned. The limited pixel area Pa (FIG. 3A) is preferably selected to include 15 pixels of the 490 pixels per image field in the "x" direction of glass web travel and the 768 pixels transverse ("y") thereto (15×768). By thus capturing a limited array or area Pa of pixels, as compared to a single line, a much deeper analysis of a particular defect can be acquired. Furthermore, the scanning is performed from a leading edge or leading pixel line Le of the 15×768 pixel area Pa in an upstream direction, as is indicated by the unnumbered arrow in FIG. 3A, which reduces scan time absent any decrease in speed, accuracy or reliability. The latter is depicted in FIG. 3A with the "apparent" defect or shadow defect acquired by the camera 11 being imaged upon the image field or pixel area 41A as simply a small mark or defect image Di. However, depending upon a particular defect, the mark Di will reflect a different number and configuration of pixel values which can be appropriately sized, classified and categorized, including the "x" and "y" locations/coordinates (FIG. 1), all of which are sent from the individual inspection module, in this case the inspection module 21 of camera 11, to the marking/logging module 45 thereof via the conductor 51. The marking and logging module 45 is another conventional computer, such as the BSI Model 486 VLB-ISA-66, individually connected to the respective inspection modules 21–24 via conductors 51–54. The marking and logging module 45 also receives line speed signals from a conventional line speed controller 55 via a line 56 to assure that if a defect is captured in one frame of any of the cameras 11–14, that defect will have moved to a specific location at a specific time in the succeeding (second) frame or imaging area 41B (FIG. 3B) and into a third and another succeeding camera frames 41C (FIG. 3C), as determined by the exactitude of inspection desire.

The fact that the defect image or shadow defect Di appears in the frame 41A of FIG. 3A of camera 11 does not necessarily indicate that there is in fact a defect in the glass web G. The defect image Di might be, for example, simply the result of a spurious electrical signal or a transient spot of dirt upon the glass web G which will shift positions during glass web movement. A defect is instead indicated by a change between successive frames or image area 41A, 41B, 41C so that once a change is detected in one frame (FIG. 3A), there is an assumption that a defect exists in the glass web G and, that defect is logged in the marking and logging module 45. In the next frame (FIG. 3B), the same defect Di, if it is in fact an actual defect, will have moved to a precise location downstream of its initial position due to the movement of the glass web G and when the next image area 41B is acquired by the camera 11 (FIG. 3B) and scanned by the downstream shifted pixel scanning area Pa', the defect Di will appear as the same defect Di' located at the same "x" and "y" coordinates as the first detected defect Di but moved in the direction "z" of glass web travel. The speed of travel of the glass web G is not only infed from the speed controller 55 via the line 56 to each marking and logging module 45 of each of the inspection modules 21–24, but the inspection modules 21–24 also have speed information transferred from the specific marking and logging module 45 to each inspection module 21 through 24 via respective lines 61–64. Therefore, when the defect image Di is acquired (41A of FIG. 3A), the speed of travel of the glass web G is known and when transferred via the line 51, the precise "x" and "y" location of the defect image Di is logged relative to glass web speed and at a delta of such speed the defect image Di, if it is a defect, will appear as the same defect Di' located in the same "x" and "y" coordinates, but obviously in a downstream position "z" from the first location. At this point, the existence of the pixel array defect Di' (FIG. 3B) at the precise location where it ought be compared to its initial detection at Di (FIG. 3A), offers a high degree of reliability that the first scanned shadow defect Di is in fact an actual defect and, if desired, a marking and sorting signal via a line 68 transfers a marking and sorting signal to a conventional marking and sorting module 70 of a conventional construction which sends signals via a line 71 to conventional glass marking machines, glass cutting machines, and/or glass sorting machines for respectively marking, cutting and/or sorting glass sheets from the glass web G.

In order to additionally increase the reliability of the inspection system, another pixel array scan Pg (FIG. 3B) is conducted in the same image field or frame 41B of FIG. 3B which located the defect image Di' by scanning the pixel array Pa to further confirm movement of the defect image Di from the position shown in FIG. 3A to the position shown in FIG. 3B. If, for example, the pixel array Pa detected the defect image Di but the latter occurred as a result of a piece of dirt on the background W, the piece of dirt is immobile and it would not be detected during the succeeding scan of the pixel array Pa' for the defect image Di' of FIG. 3B. However, since in the example given the apparent or assumed defect image Di was detected, the assumption is that the defect image Di moved from its detected position in the frame or image field 41A of FIG. 3A and is no longer there, i.e., there remains but a "ghost" of the defect image 41A. Thus, when the same pixel area Pa scanned in the image field 41A of FIG. 3A is scanned in the image field 41B of FIG. 3B, which is identified as "ghost" scan pixel area Pg, the pixel array Pg will not evidence a defect, merely the absence thereof, which for purposes of description is indicated as a "ghost" defect image Dig (FIG. 3B) of the now nonexistent defect image Di which is in the downstream position Di'. Obviously, by detecting, so to speak, the absence or nonexistence of the "ghost" defect image Dig by scanning the pixel array Pg, the system additionally confirms that the defect images Di and Di' detected by the scan of the pixel arrays Pa and Pa', respectively, is indeed a defect in the glass web G.

To achieve maximum confirmation within reasonable time and speed constraints a third scan of the next successive image field or frame 41C is performed, as is reflected in FIG. 3C, and in this case it is known, once again, that based upon the known "x" and "y" coordinates and the speed of glass web travel, the defect image Di' of FIG. 3B ought appear at a specific downstream location when subsequently scanned at pixel area Pa", and if such occurs, the same will be imaged as a defect image Di". In this fashion, the detection of the defect image Di' confirms the existence of an apparent defect Di and the subsequent detection of the defect image Di" virtually assures that indeed the system has found a defect, not transient dirt or a spurious signal. At the completion of the detection of the defect image Di" an appropriate signal is transmitted over the line 68 to the marking and sorting module 70 and from the latter over the line 71 to appropriate marking, glass cutting and/or sorting machines.

Thus far the inspection system has been described to the extent of assuring that a shadow defect observed by camera 11 (or any one of the remaining cameras 12–14) upon the white background W is in fact a defect on or in the glass web, as evidenced by the confirming defect images Di' and Di". However, depending upon the end use of glass sheets or sections which will eventually be cut/fabricated from the glass web G, the defect might be essentially insignificant and, therefore, ought not be removed. Obviously, the converse is also true and if the defect is large or small but its removal is appropriate for the end use intended, the removal thereof by appropriate downstream cutting of the glass web Ge is dictated. Thus, the invention proceeds beyond merely assuring the presence of a defect on or in the glass web G by further analyzing the defect image Di' or Di" via the marking and logging module 45. Since the defect image Di might not be a defect, analysis thereof is inappropriate, and it is only upon achieving the confirming imaging defect Di' that further analysis takes place, although the further analysis preferably takes place after the detection of the imaging defect Di".

Figure 4:
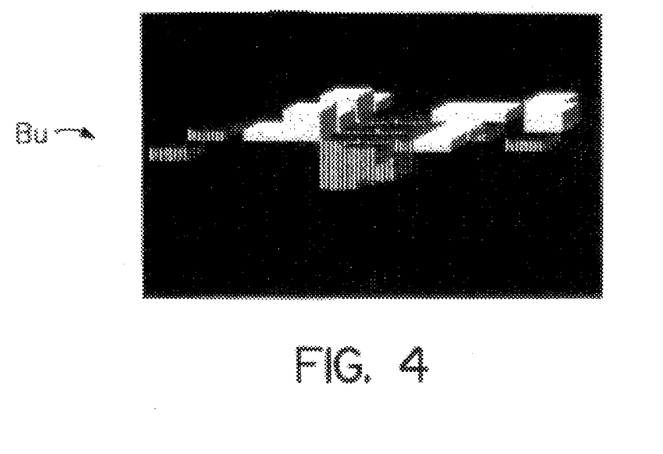
FIGS. 4 and 5 are perspective views, and illustrate respective "bubble" and "stone" defects as represented by three-dimensional pixel groups or arrays upon a screen of the inspection module or PC computer associated with each CCD camera.

As was noted earlier, the defect images Di, Di' and Di" are all defined by selective groups of pixels within each scanned pixel area Pa, Pa' and Pa". Depending upon the particular defect, these detect images Di, Di' or Di" are of a particular size and configuration, a particular brightness and/or darkness, etc. FIG. 4 reflects a three-dimensional group of pixels or pixel plot indicative of the defect Di, Di' or Di". It is assumed that the defect resulting in the defect image Di, Di' and/or Di" is a bubble Bu illustrated in the three-dimensional pixel plot in FIG. 4. The analysis of the pixels and groups of pixels of the defect images Di, Di' and/or Di" involves a degree of artificial intelligence to achieve recognition of a specific type defect, be it a glass bubble, seed, etc. However, after analyzing thousands of pixels and groups of pixels, various characteristics of pixel groups lend themselves to a high degree of probability that a particular pixel group is reflective of a particular glass defect. For example, bubbles Bu are slightly bright, dark, then slightly bright again, causing an appearance of a "hole" with a ring around it, as depicted in FIG. 4. Small bubbles are projectable as large bubbles, but open bottom bubbles have a projectability factor of about two times that of a "body" (glass web encapsulated) bubble.

Figure 5:
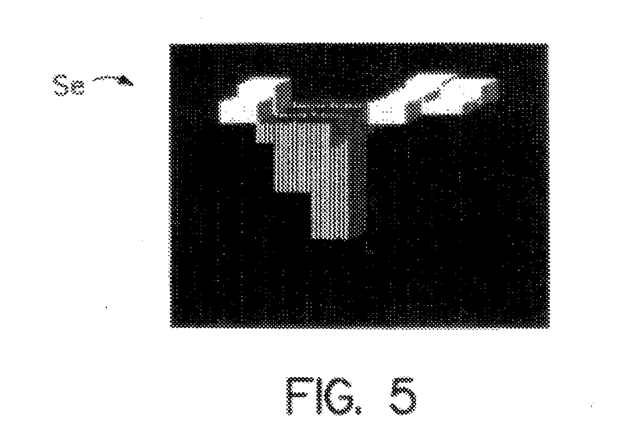

As another example, a seed Se appears in the three-dimensional pixel plot of FIG. 5 and, though somewhat similar to the bubble Bu, has more darkness in the middle shadow and little to no bright area around it. Seeds Se are also always very small. The seed Se of FIG. 5 is, for example, approximately 0.5 mm (0.021 inch) in size, whereas the bubble Bu of FIG. 4 is approximately 1.7 mm (0.066 inch) in size. Thus, by studying virtually thousands of shadow defects and their three-dimensional pixel arrays, different defects call be categorized and thereby a decision made as to whether a particular defect warrants ifs removal from a glass web G. Among the characteristics which have been analyzed and utilized to create sufficient artificial intelligence for glass defect classification purposes are (1) the projectability of a glass defect, namely, the relative darkness or brightness of the glass defect:
(2) the total light change in the scanned pixel area created by the glass defect;
(3) a total count of the number of pixels involved in the pixel group of a particular glass defect:
(4) whether changes in the pixel group are positive or negative in all coordinate directions:
(5) the number of pixels which change to bright versus a ratio of how many pixels were bright versus how many pixels were dark within a pixel group;
(6) the sharpness of the change and/or shape of the change, long and thin, versus high and wide. etc.: and
(7) the number of bright peaks and dark peaks in a pixel group, etc.

The totality of the latter information is evaluate and a mathematical number is given to each of the specific items just described and a classification is determined based upon the combination of these criteria to mark or not mark, cut or not cut and/or sort or not sort the glass via the marking and sorting module 70.

In keeping with the foregoing, the present inspection system consistently categorizes glass defects down to 0.1 mm in size and has demonstrated a unique sensitivity to all known defects, including stones, bubbles, seeds, scratches, and the like, while doing so absent the need to wash the glass web. The system discriminates between dust, ash, etc. on the one hand and glass defects on the other, and does so while at the same time eradicating false "positive" readings. The system is insensitive to background inconsistencies, including but not limited to broken glass, spilled ink, cigarette butts, etc. and to an overall change in brightness level caused by AC fluctuations as high at ten percent. Furthermore, by appropriate calibration and position marking of the physical glass web in both "x" and "y" coordinates, defect removal can be achieved with a minimum of waste or scrap.

Reference is again made to FIG. 1 and the overlapping scanning portions 01–2, 02–3 and 03–4. If a defect occurs in any one of these areas, it will, of course, be detected by at least two cameras 11, 12 or 12, 13 or 13, 14. However, this double detection, so to speak, has no bearing upon the overall operation of the inspection system. For example, if the defect Di were located in the overlapped scanning portion 01–2 of FIG. 1, the same would be observed/scanned by the cameras 11, 12 and each of the cameras 11, 12 would input its acquired image field or frame to the respective inspection modules 21, 22. The defect Di so detected by the camera 11 in the scanning portion 01–2 would be processed exactly as that described relatives to FIGS. 2 through 3C, although its location would essentially be shifted in the "y" direction relative to the glass web G and its location in each of the image fields 41A–41C. Basically the defect image Di, Di' and Di" of FIGS. 3A through 3C would be shifted to the right, as viewed in the latter figures adjacent the right-most edge (unnumbered) of these image fields. Though not illustrated, the same defect images Di, Di' and Di" would be located adjacent the left hand edge (unnumbered) of the image fields succeeding the image field 42 of FIG. 2, and these would be processed identically as that described relative to FIGS. 3A–3C. In this fashion, the marking and locking module 45 would receive and transmit duplicate signals to and from the inspection modules 21, 23, respectively, and the marking and sorting module 70 to either mark or not mark, but or not cut and/or sort or not sort the glass containing the defect in the overlapped scanned portion 01–2.

While the inspection invention has been described relative to a conventional inspection housing 11, it is to be understood that the same is obviously unnecessary and, thus, the housing 11, the floor F, the railing R and the stairs S1, S2 can be eliminated when the inspection system is automated.

In further accordance with the present invention, the cameras 11–14 and the light source 13 can be located beneath the glass web G, whereas the white background W can be located above the glass web G. So long as there is sufficient room, as there is, between the conveyor rollers CR in the direction of glass travel ("z") as there is, the scanning fields F1–F4 can be acquired.

Though not illustrated, obviously if the glass web G were instead an opaque web, such as a roll of tinplate or the like, the cameras 11–14 would not view through the opaque web and would not view a shadow defect. Instead the cameras 11–14 would scan an upper surface of the opaque web and, depending upon the defect, several options are available. For example, if the opaque web is illuminated from beneath and scanned from above by the cameras 11–14, the light passing through a "pin hole" would be detected as a defect image bearing in intensity from the nominal (darker) image field of the imperforate opaque web.

As another example, if the glass web G were opaque aluminum foil, the same would be viewed from above by the cameras 11–14 and the aluminum foil absent defects would have a nominal reflected light value. However, scratches, folds, tears would alter any such nominal value and alter the reflected light detected by the cameras 11–14 and transmitted to the respective inspection modules 21–24 for eventual processing in the manner heretofore described. Thus, while the inspection process has been described with respect to its preferred embodiment, the same is equally applicable to many variations therein, including the inspection of individual transparent and opaque bodies of predetermined size and shape, as opposed to fabricated webs of indeterminate lengths, such as the glass web G.

Although a preferred embodiment of the invention has been specifically illustrated and described herein, it is to be understood that minor variations may be made in the apparatus without departing from the spirit and scope of the invention, as defined the appended claims.

What is claimed is:

1. A method of inspecting a moving transparent body comprising the steps of moving a transparent body along a predetermined path of travel in a predetermined direction at a predetermined speed, detecting for the presence of a defect in or upon the transparent body indicative of a first defect location at a first position of transparent body movement, subsequently detecting for the presence of the same defect in or upon the transparent body at a second position of transparent body movement downstream of said first position along said predetermined path of travel indicative of a second defect location at said second position thereby confirming by the detected presence of a defect at the second defect location the existence of a defect by the movement thereof between the first and second defect locations, performing the detecting steps by illuminating the transparent body by passing light through the transparent body whereby a defect in or upon the transparent body appears as a moving defect shadow, and the first-mentioned and subsequent detecting steps detect for the presence of a defect shadow at the first and second positions of body movement.

2. The inspecting method as defined in claim 1 wherein the moving body is sheet material.

3. The inspecting method as defined in claim 1 wherein the moving body is sheet material of indeterminate length.

4. The inspecting method as defined in claim 1 wherein a defect in or upon the transparent body appears as a moving defect shadow upon a background.

5. The inspecting method as defined in claim 1 wherein a defect in or upon the transparent body appears as a moving defect shadow upon a bright background.

6. The inspecting method as defined in claim 1 wherein a defect in or upon the transparent body appears as a moving defect shadow upon a white background.

7. The inspecting method as defined in claim 1 including the step of transforming the detected shadow into a group of pixel values.

8. The inspecting method as defined in claim 1 including the step of transforming the detected shadow into a group of pixel values based upon artificial intelligence.

9. The inspecting method as defined in claim 1 including the step of marking the moving transparent body in correspondence to a detected defect.

10. The inspecting method as defined in claim 1 including the step of performing a sorting operation subsequent to the performance of the subsequent detecting step.

11. The inspecting method as defined in claim 1 wherein the moving body is glass and further performing the step of cutting the glass to remove the defect in response to the confirmation of the presence of a defect at the second defect location.

12. A method of inspecting a moving transparent body comprising the steps of moving a transparent body along a predetermined path of travel in a predetermined direction at a predetermined speed, directing light through the transparent body toward a background against which a defect in or upon the transparent body will appear as a shadow, detecting for the presence of a shadow at a first shadow location upon the background which might be indicative of a defect in or upon the transparent body as the transparent body moves in the predetermined direction, subsequently detecting for the presence of the same defect in or upon the body as a second shadow at a second shadow location downstream of the first shadow location, and removing the defect from the transparent body in response to the analysis of the detected first and second shadows confirming the detected first and second shadows to be a defect in or upon the transparent body.

13. The inspecting method as defined in claim 12 wherein the analyzing step includes the step of transforming the detected shadows into a group of pixel values.

14. The inspecting method as defined in claim 12 wherein the analyzing step includes the step of transforming the detected shadows into an group of pixel values based upon artificial intelligence.

15. The inspecting method as defined in claim 12 wherein the analyzing step is based upon artificial intelligence.

16. The inspecting method as defined in claim 12 wherein the shadow presence direction steps are performed at least twice prior to the performance of the analyzing step, and the defect removing step is performed only upon the presence of the shadows being detected at two different locations along the predetermined path of travel.

17. The inspecting method as defined in claim 12 wherein the analyzing step is based upon artificial intelligence, and the defect removing step is performed only upon the detected shadows corresponding to at least one of several different artificial intelligence descriptions of a variety of different defects.

18. The inspecting method as defined in claim 12 wherein the moving transparent body is sheet material.

19. The inspecting method as defined in claim 12 wherein the moving transparent body is sheet material of indeterminate length.

20. The inspecting method as defined claim 12 wherein the moving transparent body is glass sheet material.

21. The inspecting method as defined in claim 12 wherein the moving transparent body is glass sheet material of indeterminate length.

22. The inspecting method as defined in claim 12 wherein the transparent body is glass and the removing step is performed by cutting the glass body to separate a portion of the body containing the glass defect from a remaining portion of the glass body.

23. The inspecting method as defined in claim 22 including the step of sorting the defect-containing portion of the glass body portion from the remaining glass body portion.

24. A method of inspecting a transparent body which may have a defect therein or thereon comprising the steps of moving the transparent body along a predetermined path of travel in a predetermined direction a predetermined speed, illuminating the transparent body to create a moving defect shadow of the defect, creating a succession of image fields through which a defect shadow will pass during transparent body movement and will be depicted as a defect area of light different from a nominal light area of each image field, initially scanning a first image field to detect the presence of a first detect light area at a first position which might be indicative of a defect shadow and its defect, subsequently scanning a second image field at a second position to detect the presence of the first defect light area at a downstream second position commensurate with transparent body movement established by the predetermined speed thereof, and confirming the existence of the defect upon detecting the first defect light area at the downstream position.

25. The inspecting method as defined in claim 24 wherein the successive image fields are each defined by art area of pixels.

26. The inspecting method as defined in claim 24 wherein the successive image fields are each defined by an area of pixels, and each scanning step is performed by scanning a limited pixel area of each scanned image field.

27. The inspecting method as defined in claim 24 wherein the successive image fields are each defined by art area of pixels, and each scanning step is performed by scanning a downstream leading edge of a limited pixel area of each scanned image field and continuing the scanning of each limited pixel area in an upstream direction.

28. The inspecting method as defined in claim 24 wherein the successive image fields are each defined by an area of pixels, and each scanning step is performed by scanning a downstream leading pixel line of a limited pixel area of each scanned image field and continuing the scanning of pixel lines of each limited pixel area in an upstream direction.

29. The inspecting method as defined in claim 24 wherein during the performance of the subsequent scanning step, the second image field is scanned to establish the absence of the first defect light area at the first position which additionally confirms the existence of a defect by virtue of defect movement.

30. The inspecting method as defined in claim 24 wherein the successive image fields are each defined by an area of pixels, each scanning step is performed by scanning a limited pixel area of each scanned image field, and the first defect light area is analyzed by at least one of (a) determining the ratio of light change between the first defect light area and the nominal light area of the associate image field, (b) determining the size area of the first defect light area, (c) determining the length and width of the first defect light area, (d) determining the number of bright peaks and light peaks of the first defect light area, and (e) determining the sharpness of the first defect light area.

31. The inspecting method as defined in claim 24 wherein the transparent body is a sheet of glass, and further performing the step of selectively cutting the glass sheet to separate a defect-containing portion of the glass sheet from a remainder of the glass sheet.

\* \* \* \* \*